United States Patent
Nilo et al.

(10) Patent No.: US 7,241,144 B2
(45) Date of Patent: Jul. 10, 2007

(54) METHOD OF BONE EXPANSION AND COMPRESSION FOR RECEIVING A DENTAL IMPLANT USING THREADED EXPANDERS

(75) Inventors: Patricio Nilo, Pembroke Pines, FL (US); Bruce L. Hollander, Boca Raton, FL (US)

(73) Assignee: Bio-Lok International, Inc., Deerfield Beach, FL (US)

( * ) Notice: Subject to any disclaimer, the term of this patent is extended or adjusted under 35 U.S.C. 154(b) by 151 days.

(21) Appl. No.: 10/630,478

(22) Filed: Jul. 30, 2003

(65) Prior Publication Data

US 2005/0026114 A1    Feb. 3, 2005

(51) Int. Cl.
*A61C 8/00* (2006.01)
*A61C 3/02* (2006.01)

(52) U.S. Cl. .................. 433/174; 433/141; 433/165

(58) Field of Classification Search ........ 433/172–176, 433/165, 141
See application file for complete search history.

(56) References Cited

U.S. PATENT DOCUMENTS

| 5,259,398 | A | * | 11/1993 | Vrespa ....................... 128/898 |
| 5,795,160 | A | * | 8/1998 | Hahn et al. ................. 433/174 |
| 5,997,298 | A | * | 12/1999 | Nowak ....................... 433/165 |
| 6,146,138 | A | | 11/2000 | Dalmau |
| 6,887,077 | B2 | * | 5/2005 | Porter et al. ................ 433/174 |
| 2002/0094508 | A1 | * | 7/2002 | Lorenzi ...................... 433/165 |

\* cited by examiner

Primary Examiner—John J Wilson
(74) Attorney, Agent, or Firm—Melvin K. Silverman; Yi Li

(57) ABSTRACT

A method and devices for bone tissue expansion and compression for receiving a dental implant are disclosed. The method includes the steps of creating an initial osseotomy site in the maxilla or the mandable using a pilot drill; screwing a first threaded expander into the site to expand the site laterally; and allowing the expander staying in the site for a short time to impress the interior wall of the osseotomy site; then retrieving the first expander. These steps are repeated using a second, and/or third threaded expander having an increasing outer diameter to further expand the osseotomy site to a final diameter which is complementary, but narrower than the diameter of the dental implant so that expanded osseotomy site enables uniform engagement of the implant with the bone tissue. A preparation drilling to extend osseotomy site only at cortical level can be incorporated for hard bone and larger implants.

21 Claims, 1 Drawing Sheet

METHOD OF BONE EXPANSION AND COMPRESSION FOR RECEIVING A DENTAL IMPLANT USING THREADED EXPANDERS

FIELD OF INVENTION

The present invention relates to a method and devices for expanding and compressing bone for receiving a dental implant. More specifically, the present invention relates to a method of using a series of threaded expanders to gently expand an osseotomy site as an alternative to removal of bone by drilling and tapping by osteotome.

BACKGROUND OF THE INVENTION

Dental implants are used to secure a prosthetic received and other dental items in the oral cavity. One of the important goals of implant therapy is to achieve a firm, durable, intra-oral connection to the maxilla and mandable with a screw-type or cylinder-type structure made of a biologically compatible material. However, implant placement is often compromised by the quality of bone and available ridge width.

The creation of an osseotomy site for placement of implants by means of drilling is well known in dentistry. However, valuable bone tissue is removed during drilling, consequently fitting strength of an implant is not guaranteed, particularly when the surrounding bone issue is soft and porous. The bone tissue can be categorized into various bone classes. It is well known in dentistry that the bone of the upper jaw, or the maxilla, is considerably softer than the bone of the lower jaw, or the mandable. The bone of the upper jaw can be compared with balsa wood in terms of its strength. Osteoporosis, the structural change of the bone tissue due to age, also results in porous and soft bones. The drilling for the formation of osseotomy sites in the upper jaw for implant placement proves to be unfavorable, since bone tissue is removed from the soft bone. In the case of a narrow ridge, available bone tissue and bone density are critical to the quality of the resulting implant placement.

The alternative non-drilling devices and methods presently used for preparing osseotomy site for placement of dental implant are based, to a large degree, on an instrument named osteotomes. Osteotomes, developed by Dr. Summers in late 1980, comprises a handle-like holder and a shaft with a working tip having a circular cross section, and it has the shape of a graduated round rod. Osteotomes are available in several sizes with increasing diameters. They are frequently used by dentists to perform a required bone expansion for placing a dental implant.

In use, the working tip of the osteotome is placed on the bone base and the osteotome is introduced by tapping the top of the osteotome with a mallet or small hammer. As the introduction of the osteotome progresses, the next largest instrument is inserted into the osseotomy site formed. The implant bed is created by means of expanding and compressing the bone tissue. The working end of osteotome can be concave or round. The penetration depth of the osteotome is determined by means of markings. By pressing in the dental instrument to form the osseotomy site, the bone tissue of the jaw is displaced and compacted for receiving the dental implant. After implant placement, new bone tissue is formed around the implant. Therefore, no bone tissue is removed using osteotome technique, instead the bone tissue, especially the soft bone is compacted.

Comparing to drilling procedure, osteotome technique has many advantages. The compacted surrounding bone tissue prepared by osteotome method has higher bone density. The use of osteotomes allows implant placement in areas of limited bone width; improves initial implant stability and implant success in maxilla. It has been reported that the osteotome technique increases new bone formation and leads to an enhanced osseointegration of dental implants in jaw bones.

However, the osteotome technique is also a traumatic technique, consequently, it is accompanied by various disadvantages. Among the most important disadvantages, one is the damage to the bone, up to and including breaking and chipping of the bone, as a result of tension created at the dental base with each tap of the small hammer onto the osteotome. In some instances, a complete deterioration of the dental base can occur, and this deterioration of the dental base requires extensive repairs. Another disadvantage is the formation of simple, slightly conical cavities in the jaw, which does not provide a reliable bed for the fixation especially of screw-type implants. Since implants have different outer contours, particularly graduated cylinder implants with screw threads, the smooth, slightly conical osseotomy site formed in the jaw by osteotome is not structurally complementary to the threaded implants. This can results in difficulty in the osteointegration and difficulty in the cohesion based on an incomplete contact between the implant and bone. A further disadvantage is the alignment defect of the fixation axis because the bone expansion can not be controlled or adjusted. An additional disadvantage is the appearance of a hammer, the shock of the hammer on the metal and resulting fear of the patients.

U.S. Pat. No. 6,146,138 (to Dalmau) discloses a non-traumatic expansion device and a method of use. The expansion device has a threaded end having a shape of an elongated cone. The thickness of the threaded head is dependent on an expansion to be required. This device has the function of a screw for the purpose of drilling bone and keeping the bone mass. However, the screw threads do not correlate to the implant structure, and the prepared bed does not ensure proper implant contact into surrounding bone issues. If the implant thread does not match the expander, the bone will be pulverized by the implant threading into the site.

Because of the above described disadvantages, there exists a strong need for the development of new devices and methods which can reduce the problems associated with the existing techniques, and improve the techniques of bone expansion to achieve a better quality of dental implant therapy.

SUMMARY OF THE INVENTION

In one aspect, the present invention relates to a series of threaded bone expanders of the same threaded structure, with increasing diameters, for expanding bone for receiving a dental implant. The threaded expander has a one-piece structure, which comprises a top for engaging with a dental ratchet, a cylindrical shaft, a transition between the upper end of the cylindrical shaft and the top, and a threaded expansion tip connected to the lower end of the cylindrical shaft.

In a further aspect, the present invention relates to a method of expansion of bone tissue for receiving a dental implant. The method comprises the steps of creating a small initial osseotomy site in the maxilla or the mandable to a desired depth using a pilot drill at a predetermined implant location; screwing a first threaded expander into the osseotomy site, thereby expanding the osseotomy site laterally; allowing the first expander staying in the osseotomy site for a sufficient amount of time to impress an interior wall of the osseotomy site; retrieving the first expander by screwing the first expander out in a reverse direction; and repeating the expansion steps using a second threaded expander which has an increasing outer diameter and a substantially same thread structure to the dental implant, to further expand the osseotomy site laterally to a final diameter which is complementary, but narrower than an outer diameter of the dental implant so that expanded osseotomy site enables the implant to sufficiently bite into and uniformly engage with surrounding bone tissue. Each expander and the implant are carefully started following the thread of the previous expander.

Furthermore, additional preparation steps can be incorporated in the instant method for preparing hard bone tissue and for receiving large dental implants.

It is an object of the present invention to provide improved threaded bone expansion devices which provides a gentle expansion of bone tissue at the implant site; wherein the devices can be handled conveniently by existing dental tools used for placing implants.

It is another object of the present invention to provide a method of sequential expansion of bone tissue using a set of threaded bone expansion devices to provide an implant site which has a complementary structure and dimensions to the implant to be placed, so that the implant receives an optimal support from and optimal engagement with surrounding bone tissue.

The above and yet other objects and advantages of the present invention will become apparent from the hereinafter set forth Brief Description of the Drawings and Detailed Description of the Invention.

DETAILED DESCRIPTION OF THE INVENTION

In one aspect, the present invention provides a set of threaded bone expanders of the same threaded structure, with increasing diameters, for expanding bone, particularly of the narrow ridge, for receiving a dental implant. The threaded expander set can be used in combination with existing ridge expanding/splitting techniques allowing gentle expansion of the osseotomy site. The osseotomy site is an opening in the maxilla or the mandable for placement of a dental implant.

Figure 1:
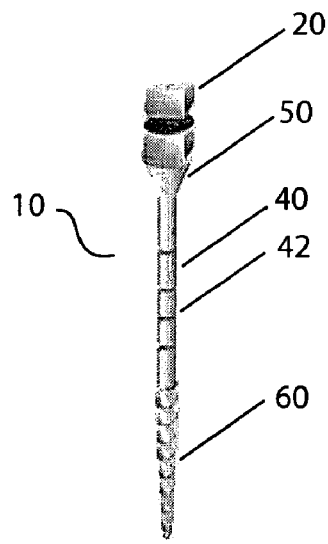
FIG. 1 is a perspective view of a first threaded bone expander of one embodiment of the present invention.

In one embodiment, as shown in FIG. 1, the threaded expander 10 has an one-piece structure, which comprises a top 20 for engaging with a dental ratchet, a cylindrical shaft 40, a transition 50 between cylindrical shaft 40 and top 20, and a threaded expansion tip 60 connected to cylindrical shaft 40. The expander 10 can be made of stainless steel or other suitable materials used in dentistry.

The top 20 of the expander 10 is the similar to the hex top in terms of function for engaging with a ratchet. As one example shown in FIG. 1, the top 20 has a square shape. However, other suitable geometries, such as rectangular, triangular, can also be used.

Figure 2:
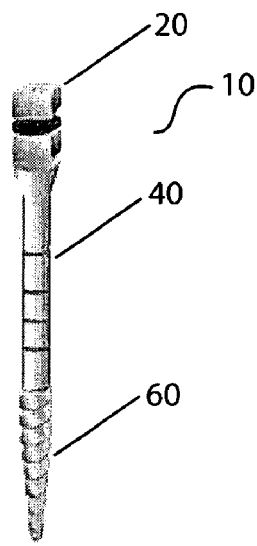
FIG. 2 is a perspective view of a second threaded bone expander of one embodiment of the present invention.
Figure 3:
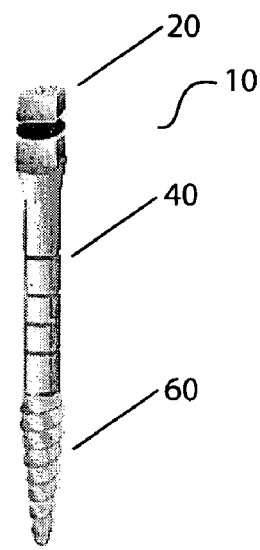
FIG. 3 is a perspective view of a third threaded bone expander of one embodiment of the present invention.

A set of expanders consists of a series of threaded bone expanders 10, each of which has a similarly designed body, length and shape, with diameters at the apical end ranging from 2.5 to 7.5 mm. There can be five or more threaded expanders 10 within a set, for most common procedures applied to the dental implants. As shown in FIG. 1 to 3, from the first to the third expanders, the width of the threaded expansion tip 60 and cylindrical shaft 40 increase sequentially. The same continues to the fourth and the fifth expanders. The transition 50 complements the width increase of the cylindrical shaft 40 among the set. For example, for a small cylindrical shaft 40 and threaded expansion tip 60 the transition 50 has a larger angle of inclination. The inclination reduces with the increase of the cylindrical shaft 40. Therefore, a common top 20 is used for all expanders in the set. In one example, the first, second, third, fourth and fifth expanders have outer diameters of about 2.8 mm, about 3.1 mm; about 3.4 mm; about 4.0 mm; and about 5.5 mm, respectively. The outer diameter is defined as the diameter at the apical end of the threaded expansion tip 60.

In one embodiment as shown in FIG. 1 to 3, the threaded expansion tip 60 is tapered. Other suitable shapes, such as other shapes of inclination and straight, can also be used, as long as the shape of the threaded expansion tip is substantially a mirror image of the implant to be placed.

Independent from the diameter, all expanders 10 within one set have the same length, and the threaded expansion tip 60 of each expander within one set has the same length. However, different sets of expanders can have different lengths to accommodate implants of various lengths, i.e., implants from 8.0 to 18.0 mm in length. The cylindrical shaft 40 has a plurality of markings along the longitudinal axis of the shaft for indicating the depth of the expander during preparation of an osseotomy site. Typically, the marking depicts the implants with 8, 10, 11.5, 13 and 15 mm depth marking. The marking can also be specifically made to meet the requirement of an implant system.

In a preferred embodiment, the threaded expansion tip 60 has substantially the same threaded structure to the dental implant to be placed. However, more importantly, it is the last expander, used prior to the placement of the implant, which has substantially the same threaded structure to the dental implant to be placed. The first and second expanders are more used for initial and/or intermediate expansions. The third, fourth and fifth expanders, each selected based on the size of the implant, are more for the last expansion prior to the placement of the implant.

As an important feature of the present invention, the outer diameter of the last expander is slightly narrower than the outer diameter of the implant to be placed. Therefore, the osseotomy site prepared by the expander of the present invention enables a sufficient implant biting into the surrounding bone tissue. In a preferred embodiment, the outer diameter of the last expander is about 0.2 to about 0.5 mm narrower than the outer diameter of the implant. For example, for a dental implant of 5.5 mm, the outer diameter of the expander can be around 5.25 mm.

As an example, the threaded expansion tips 60 of the instant expanders can be made into the same structure as the threaded implants commercially available under the trade name of Silhouette™ from Biolok International, Inc., Deerfield Beach, Fla., except that the outer diameter is about 0.2 to about 0.5 mm narrower than the outer diameter of the corresponding implant. The structure of Silhouette™ implants have been described fully in U.S. Pat. No. 6,406,296, which is incorporated herein as reference in their entirety.

In a further aspect, the present invention provides a method of expansion of bone tissue for receiving a dental implant using the threaded expanders described above. The method includes following steps:

A. Create a small initial osseotomy site in the jawbone to a desired depth using a pilot drill at a predetermined location. This step is the same as the conventional drilling with a pilot drill. The range of pilot drill can be from about 1.5 mm to about 2.5 mm.

B. Screw the first threaded expander into the osseotomy site, thereby expanding the osseotomy site laterally by pushing bone issue away radially from a longitudinal axis of the osseotomy site. This is also referred to as lateral expansion. Preferably, the first expansion expands the diameter of the osseotomy site from about 0.4 mm to about 0.7 mm. The expander can be screwed in using a ratchet commonly used in dentistry.

C. Allow the first expander staying in the osseotomy site for a period of time to impress the interior wall of the osseotomy site. The time can be in a range from about 10 seconds to about 2 minutes, preferably about 1 minute.

D. Retrieve the first expander by screwing out in a reverse direction. After retrieving the expander, the interior wall of the osseotomy site remains grooves which are complementary to the structure of the expander. This is fundamentally different from the osseotomy site created by the known osteotome technique where the interior wall of the osseotomy site is smooth without grooves.

E. Repeat steps B through D using the second threaded expander, following the tread pattern already created with the first expander. This step further expands the osseotomy site laterally. Preferably, the second expansion expands the diameter of the osseotomy site from about 0.6 mm to about 0.9 mm.

F. Repeat steps B through D using the third threaded expander, following the tread pattern already created with the second expander. This step expands the osseotomy site laterally to a final diameter which is complementary, but narrower than an outer diameter of the dental implant to be placed so that the expanded osseotomy site enables the implant to sufficiently bite into and uniformly engage with the surrounding bone tissue. Preferably, the final diameter of the osseotomy site is about 0.2 to about 0.5 mm narrower than the outer diameter of the implant to be placed.

G. Screw the implant into the expanded osseotomy site, following the tread pattern already created with the second expander.

It is important that in the process described above, each expander, as well as the implant, is carefully started following the thread created by the previous expander in order to achieve the complementary structure to the implant to be placed.

Figure 4:
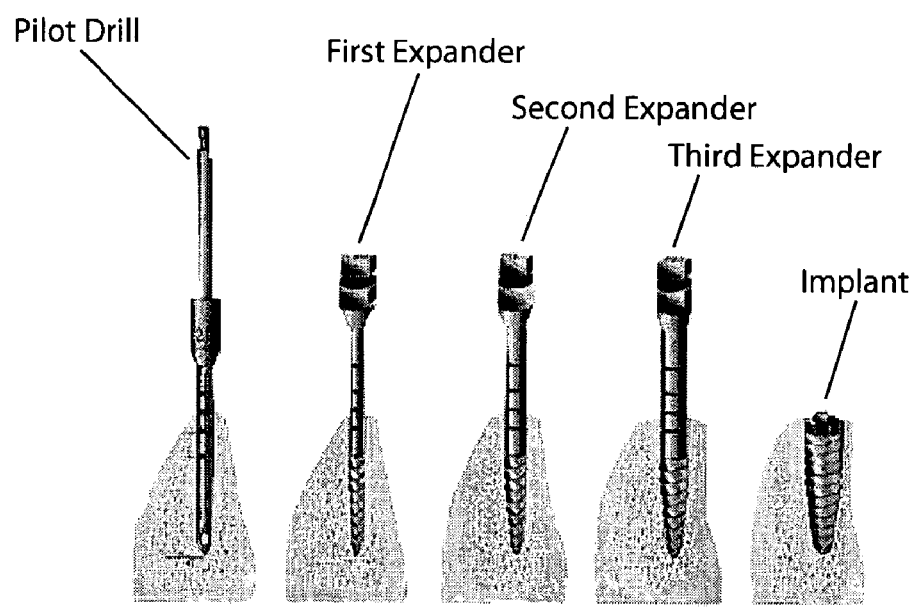
FIG. 4 is a schematic view of an initial drilling and sequential expansions of an implant site using the devices of FIG. 1 to 3, and the placement of the implant into the prepared site.

FIG. 4 illustrates pictorially the process described above, using the first, second and third expanders and the placement of the implant into the expanded osseotomy site. It can be readily appreciated from the illustration the structural similarity between the expanders and the implant, and the resulted optimal receiving environment for the implant.

If the bone tissue of the implant site under preparation is soft, the step E may be skipped. In this case, one can use a two-step expansion directly from the first expander to the third expander, instead of a three-step expansion described above. In the two-step process, the second expansion can expand the diameter of the osseotomy site more than 10 mm. The above described first, second and third expanders, with an outer diameter from about 2.8 mm to about 3.4 mm, are suitable for the three-step or two-step process described above.

In a further embodiment of the present invention, additional preparation steps can be incorporated prior to applying the expanders. This can be desirable in the case of hard bone tissue or placement of large dental implants, such as implants of 4 mm and larger. One of the additional preparations is additional drilling after the initial pilot drill to extend the size of osseotomy site for receiving a large implant. Another type of preparation is one or more drilling to extend the entrance of the initial osseotomy site only at the cortical level to a diameter complementary to the dental implant to be placed. Subsequent to the additional preparation step, a two-step or a three-step expansion using the expanders of the present invention as described above can be applied prior to placement of the implant. With this process, large implants, such as 4 mm and 5 mm implants, can be placed into the expanded and compacted osseotomy site, without difficulty of handling the hard bone crest. The fourth and fifth expander described previously can be used for the final expansion for the large implants. Drilling of the cortical plate can be achieved using conventional drills, such as twist drills.

The bone expansion method of the present invention has various advantages. Using the instant threaded expanders with increasing diameters to sequentially expand the osseotomy site achieves the similar bone compression and expansion as the osteotome techniques does. The resulted surrounding bone tissue has higher density, and it provides a stronger support for the implant, hence improves initial implant stability. Comparing to osteotome, however, the method of the present invention is a gentle and progressive approach. The introduction of the instant expander into the osseotomy site is similar to the introduction of a screw type implant, which is a well established dental procedure. It is easier to maintain proper alignment when one screws in the expanders progressively, therefore, it reduces the risk of misalignment of the osseotomy site associated with osteotome method during expansion. The method of the present invention completely avoids tapping, and reduces the tension and traumatic impact on the bone and surrounding structure generated by the osteotomes. Furthermore, the bone expansion and compression achieved using the expanders of the present invention are more uniform than those achieved using osteotomes.

More importantly, the method of using the threaded expanders which have substantially same structural features of the implant to be placed generates a structurally complementary receiving site for the implant. Different from the implant site prepared by osteotomes and threaded expanders of the known prior art, the bone density of the interior wall of the osseotomy site is uniform including the complementary grooves and threads. Further, and importantly the instant method provides a final diameter of the osseotomy site narrower than the outer diameter of the implant to be placed. This means that all grooves and threads embedded on the interior wall along the longitudinal axis of the osseotomy site are uniformly narrower than those complementary elements of the implant. Such an implant site allows the implant to sufficiently and uniformly bite into and engage uniformly with the surrounding bone tissue. It will be well appreciated by those skilled in the art that such a complementary structure of the implant site and the uniform engagement arrangement can provide an optimal support to the implant. Accordingly, the method of the present invention, superior to the known techniques, can lead to a further improvement of implant stability and an enhancement of subsequent osteointegration.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

What is claimed is:

1. A method of expansion of bone tissue for receiving a dental implant comprising the steps of:
   (a) creating an initial osseotomy site in the maxilla or the mandable to a desired depth by drilling using a pilot drill at a predetermined implant location; said initial osseotomy site having a first diameter substantially smaller than an outer diameter of said dental implant;
   (b) providing multiple threaded expanders of substantially same structure with increasing diameters, each of said threaded expanders comprising: a top enabling engagement with a dental ratchet; a cylindrical shaft having a upper and a lower end, having depth markings along a longitudinal axis of said shaft; and a threaded expansion tip connected to said lower end of said cylindrical shaft; said threaded expansion tip of each of said multiple threaded expanders having a same length and a substantially same threaded structure to a threaded structure of said dental implant, yet a narrower outer diameter than said outer diameter of said dental implant;
   (c) screwing said threaded expansion tip of a first threaded expander into said initial osseotomy site, thereby expanding said initial osseotomy site laterally by pushing bone tissue away radially from a longitudinal axis of said initial osseotomy site, to obtain an once expanded osseotomy site that has a second diameter larger than said first diameter of said initial osseotomy site;
   (d) allowing said threaded expansion tip of said first expander staying in said once expanded osseotomy site for a sufficient amount of time to impress an interior wall of said once expanded osseotomy site to form grooves and threads;
   (e) retrieving said first expander by screwing said threaded expansion tip of said first expander out in a reverse direction; and
   (g) repeating steps (c) to (e) using a second threaded expander which has an increasing outer diameter and a substantially same threaded structure to said dental implant, starting by following a thread pattern created in steps (c) to (e), to further expand said second diameter of said once expanded osseotomy site laterally to a final diameter to obtain a twice expanded osseotomy site, wherein both said grooves and threads are expanded substantially from said first diameter of said initial osseotomy site; and said twice expanded osseotomy site has a complementary geometry to said dental implant, and both said grooves and said threads on said interior wall of said twice expanded osseotomy site are uniformly narrower than diameters of complementary elements of said dental implant so that said twice expanded osseotomy site enables said implant to sufficiently bite into and uniformly engage with surrounding bone tissues.

2. The method of claim 1 further comprising screwing said dental implant into said twice expanded osseotomy site after step (g), starting by following said thread pattern created by said expanders.

3. The method of claim 1, wherein in step (d) said sufficient amount of time is from about 10 seconds to about 2 minutes.

4. The method of claim 3, wherein in step (g) said final diameter is from about 0.2 to about 0.5 mm narrower than said outer diameter of said dental implant.

5. The method of claim 4 further comprising an additional step of repeating step (g) using a third threaded expander having an increasing outer diameter from said second expander to further expand said twice osseotomy site.

6. The method of claim 4, wherein said first diameter of said initial osseotomy site is in a range from about 1.5 mm to about 2.5 mm obtained using said pilot drill having a matching diameter.

7. The method of claim 6, wherein a first expansion achieved by said first expander expands said initial osseotomy site by about 0.2 to about 0.5 mm in diameter to obtain said second diameter of said once expanded osseotomy site.

8. The method of claim 7, wherein a second expansion, achieved by using said second expander expands said once osseotomy site by about 0.8 mm to about 1.2 mm in diameter to obtain said final diameter of said twice expanded osseotomy site.

9. The method of claim 1, wherein said screwing said expanders into said osseotomy site is performed using a ratchet.

10. A method of expansion of bone tissue for receiving a dental implant comprising the steps of:
    (a) creating an initial osseotomy site in the maxilla or the mandable to a desired depth by drilling using a pilot drill at a predetermined implant location; said initial osseotomy site having a first diameter substantially smaller than an outer diameter of said dental implant;
    (b) applying an additional drilling to extend an entrance of said osseotomy site only at a cortical level to a diameter complementary to an outer diameter of said dental implant;
    (c) screwing a threaded expansion tip of a first threaded expander into said initial osseotomy site, thereby expanding said initial osseatomy site laterally by pushing bone tissue away radially from a longitudinal axis of said initial osseotomy site, to obtain an once expanded osseotorny site that has a second diameter larger than said first diameter of said initial osseotomy site;
    (d) allowing said threaded expansion tip of said first expander staying in said once expanded osseotomy site osseotomy site for a sufficient amount of time to impress an interior wall of said once expanded asseotomy site to form grooves and threads;
    (e) retrieving said threaded expansion tip of said first expander by screwing out in a reverse direction; and
    (f) repeating steps (c) to (e) using a second threaded expander which has an increasing outer diameter and a substantially same threaded structure to a threaded structure of said dental implant, starting by following a thread pattern created in steps (b) to (d), to further expand said once osseotomy site laterally to a final diameter to obtain a twice expanded osseotomy site that has a complementary geometry to said dental implant, but narrower than said outer diameter of said dental implant so that said twice expanded osseotomy site enables said implant to sufficiently bite into and uniformly engage with surrounding bone issues.

11. The method of claim 10 further comprising placing said dental implant into said twice expanded osseotomy site after step (f), starting by inserting said dental implant through said cortical level of said osseotomy site and screwing into rest of said twice expanded osseotomy site by following said thread pattern created by said expanders.

12. The method of claim 10, wherein in step (d) said sufficient amount of time is from about 10 seconds to about 2 minutes.

13. The method of claim 12, wherein in step (f) said final diameter is from about 0.2 to about 0.5 mm narrower than said outer diameter of said dental implant.

14. The method of claim 13 further comprising an additional step of repeating step (f) using a third threaded expander having an increasing outer diameter from said second expander to further expand said twice expanded osseotomy site laterally.

15. The method of claim 14, wherein said threaded expansion tip of said first, second and third expanders has a same length.

16. The method of claim 10, wherein each of said expanders has a substantially same threaded structure to said dental implant for preparing a complementary geometry of said osseotomy site for receiving said dental implant.

17. The method of claim 10, wherein each expansion achieved by one of said expander expands said osseotomy site from about 0.6 mm to about 1.5 mm in diameter.

18. A kit of bone expanders for expanding bone for dental implantation comprising:
  a threaded dental implant having a major thread diameter and a minor thread diameter; and
  (ii) plurality of threaded expanders of substantially same structure with increasing diameters, each of said expanders comprising:
  (a) a top enabling engagement with a dental ratchet,
  (b) a cylindrical shaft having a upper and a lower end, having depth markings along a longitudinal axis of said shaft,
  (c) a transition between said upper end of said cylindrical shaft and said top, and
  (d) a threaded expansion tip connected to said lower end of said cylindrical shaft, said tip having a substantially same threaded structure to a threaded structure of said dental implant, and having diameters uniformly narrower than corresponding said major thread diameter and said minor thread diameter of said dental implant, wherein said threaded expansion tip of each of said plurality of expanders has a same length.

19. The kit of bone expanders of claim 18, wherein said threaded expansion tip is tapered.

20. The kit of bone expanders of claim 18, wherein said threaded expansion tip is straight.

21. A method of expansion of bone tissue for receiving a dental implant comprising the steps of:
  (a) creating an initial osseotomy site in the maxilla or the mandable to a desired depth by drilling using a pilot drill at a predetermined implant location; said initial osseotomy site having a first diameter substantially smaller than an outer diameter of said dental implant;
  (b) screwing a threaded expansion tip of a first threaded expander into said initial osseotomy site, thereby expanding said initial osseotomy site radially to obtain an once expanded osseotomy site that has a second diameter larger than said first diameter of said initial osseotomy site by about 0.2 to about 0.5 mm;
  (c) allowing said threaded expansion tip of said first expander staying in said once expanded osseatomy site for a sufficient amount of time to impress an interior wall of said once expanded osseotomy site to form grooves and threads;
  (d) retrieving said first expander by screwing said threaded expansion tip of said first expander out in a reverse direction; and
  (a) repeating steps (b) to (d) using a second threaded expander which has an increasing outer diameter and a substantially same threaded structure to said dental implant, starting by following a thread pattern created in steps (b) to (d), to further expand said once expanded osseotomy site radially by about 0.6 mm to about 1.2 mm in diameter to obtain a twice expanded osseotomy site, wherein both said grooves and said threads are expanded substantially from said first diameter of said initial osseotomy site; and said twice expanded osseotomy site has a complementary geometry to said dental implant, and both said grooves and said threads on said interior wall of said twice expanded osseotomy site are uniformly narrower then diameters of complementary elements of said dental implant.

* * * * *